United States Patent [19]

Sharp

[11] 4,127,668
[45] Nov. 28, 1978

[54] MITICIDAL MIXTURES AND METHOD UTILIZING A MACROTETROLIDE COMPOUND

[75] Inventor: Silas S. Sharp, Wilmington, Del.

[73] Assignee: E. I. Du Pont de Nemours and Company, Wilmington, Del.

[21] Appl. No.: 843,410

[22] Filed: Oct. 20, 1977

Related U.S. Application Data

[63] Continuation-in-part of Ser. No. 746,107, Nov. 30, 1976, abandoned.

[51] Int. Cl.² .................. A01N 9/02; A01N 9/24; A01N 9/28
[52] U.S. Cl. ................................ 424/279; 424/311
[58] Field of Search ............................... 424/279, 311

[56] References Cited

U.S. PATENT DOCUMENTS 3,658,870  4/1972  Buchanan ............... 260/453 R
3,777,023  12/1973  Sagawa et al. ............ 424/214 X

OTHER PUBLICATIONS

Bellina et al., C.A. 84:70356d, 3/15/76.

*Primary Examiner*—Allen J. Robinson

[57] ABSTRACT

Miticidal mixtures containing a macrotetrolide compound represented by the formula

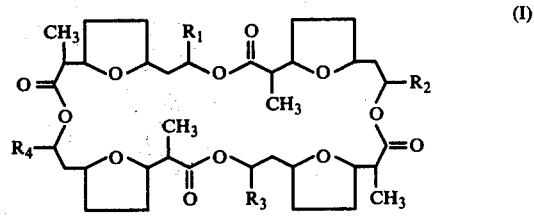

(I)

wherein $R_1$, Rd 2, $R_3$ and $R_4$ are each selected from the group consisting of ethyl and ethyl, known generically as polynactin and 2-acetoxy-3-n-dodecyl-1,4-naphthoquinone (II) exhibit improved miticidal properties when applied to plants.

3 Claims, 4 Drawing Figures

CONTROL OF TWO-SPOTTED MITES WITH COMPOUND II

CONTROL OF TWO-SPOTTED MITES WITH POLYNACTIN

CONTROL OF TWO-SPOTTED MITES WITH VARYING RATIOS OF COMPOUND II

CONTROL OF TWO-SPOTTED MITES WITH VARYING RATIOS OF POLYNACTIN TO COMPOUND II (COMPOUND II HELD CONSTANT)

MITICIDAL MIXTURES AND METHOD UTILIZING A MACROTETROLIDE COMPOUND

CROSS REFERENCES TO RELATED APPLICATIONS

This application is a continuation-in-part of my copending application Ser. No. 746,107, filed Nov. 30, 1976 (now abandoned).

BACKGROUND OF THE INVENTION

This invention relates to miticidal mixtures and method. More particularly, it relates to synergistic miticidal mixtures and method for preventing the destructive effects of pests such as mites in which a macrotetrolide compound represented by the formula

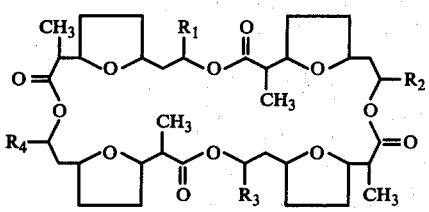

(I)

wherein $R_1$, $R_2$, $R_3$ and $R_4$ are selected from the group consisting of methyl and ethyl and known generically as polynactin is admixed with 2-acetoxy-3-n-dodecyl-1,4-naphthoquinone (II) to achieve improved miticidal properties when applied to plants in significantly smaller amounts than would be required if each of the compounds were used individually.

The prior art recognizes that certain macrotetrolide compounds may exhibit pesticidal properties individually or when combined with other compounds. U.S. Pat. No. 3,777,023 to Sagawa et al., for example, teaches that miticidal compositions of macrotetrolide antibiotics, such as polynactin, with organochloric, carbamate and organophosphorus pesticides demonstrate a higher level of miticidal activity than the macrotetrolides individually.

U.S. Pat. No. 4,055,661, moreover, teaches that 2-acetoxy-3-n-dodecyl-1,4-naphthoquinone is an effective miticide and mite ovicide.

While these references and others identify effective mite control agents, neither reference suggests that polynactin, when admixed with an amount of the particular compound 2-acetoxy-3-n-dodecyl-1,4-naphthoquinone, would result in a mixture which is synergistic, i.e., the cooperative action of the mixture of compound I and II is such that the total miticidal effect is greater than the sum of the effects of the compounds taken independently.

SUMMARY OF THE INVENTION

According to this invention it has been discovered that a mixture of

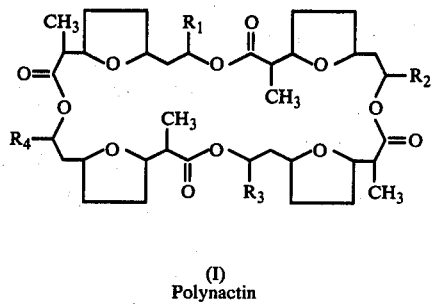

(I)
Polynactin wherein $R_1$, $R_2$, $R_3$ and $R_4$ are each selected from the group of methyl and ethyl with

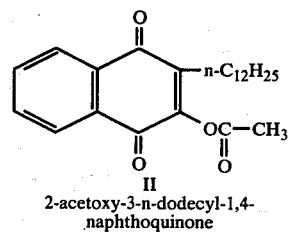

II
2-acetoxy-3-n-dodecyl-1,4-naphthoquinone is able to control mites in significantly smaller amounts than would be required if each of the compounds were to be used individually. Thus, a synergistic effect for controlling mites is unexpectedly achieved when compound (I) is admixed with compound (II) and applied to plants using known techniques. By synergistic effect it is meant that the cooperative action of mixtures of compounds (I) and (II) is such that the total effect is greater than the sum of the effects of the compounds taken independently.

DETAILED DESCRIPTION OF THE INVENTION

Figure 1:
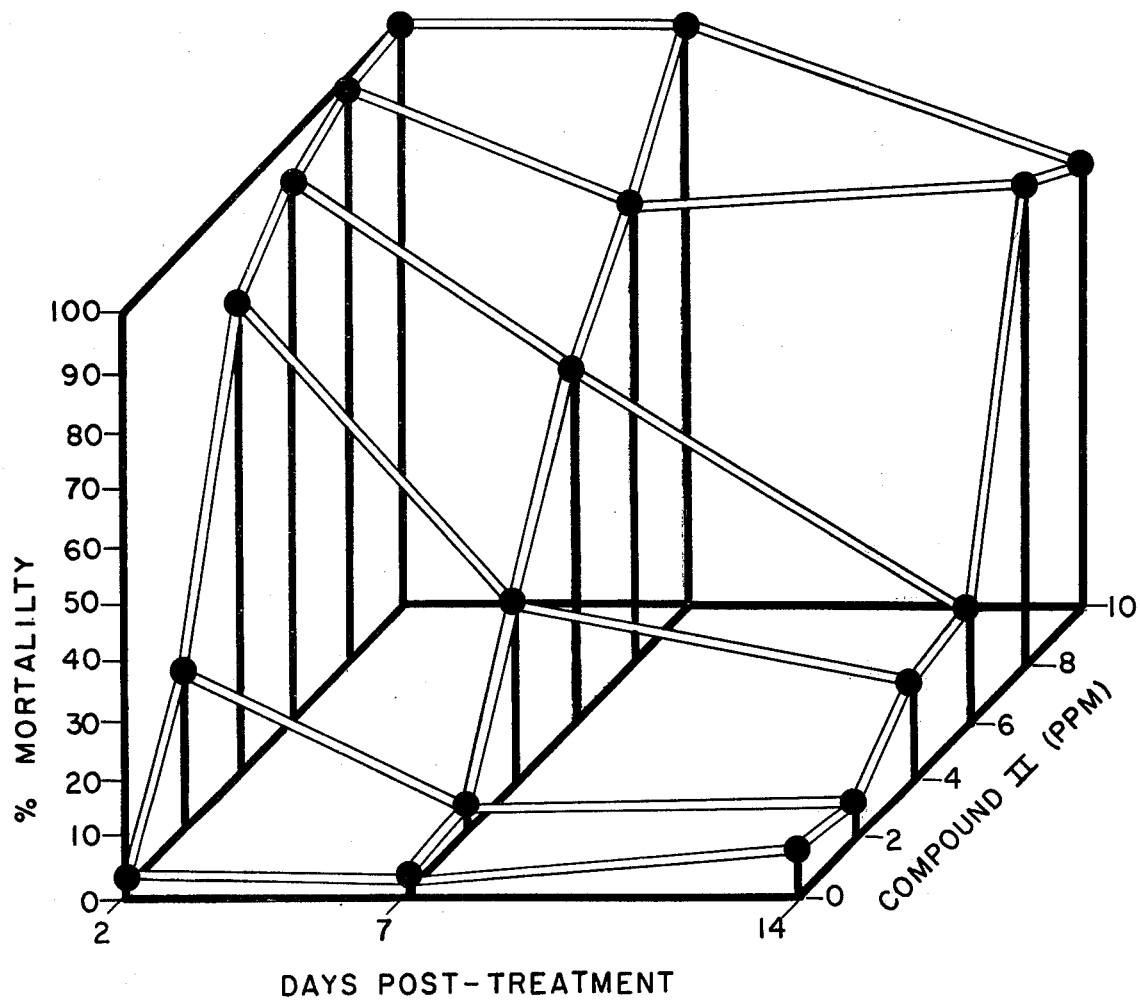
FIG. 1 is a three-dimensional graph showing mite mortality observed when compound (II) was applied individually to mite-infested plants.

Polynactin consists primarily of the antibiotic tetranactin which is produced by a strain of *Streptomyces aureus*. Four related antibiotics, known generically as nonactin, monactin, dinactin and trinactin are present as minor compounds. The physical and chemical properties and method for preparing polynactin are disclosed in U.S. Pat. No. 3,777,023, the teachings of which are incorporated herein by reference.

In the mixtures of this invention suitable for use as mite control agents, the ratio of compound (I) to compound (II) may range from 1:10 to 10:1, preferably from 1:5 to 5:1, and in the most preferred embodiment from 1:3 to 3:1. Ratios are by weight.

The miticidal mixtures of this invention may be applied to plants as sprays or dusts. Ordinarily, however, sprays are used for efficiency and convenience. The sprays may be applied as a light film over plant leaves or to run-off. It is generally desirable to wet plant foliage thoroughly since this assures contact of the miticidally effective compounds with all stages of mites present and greatly enhances the degree of control obtained.

In high volume applications, combined sprays of 2-acetoxy-3-n-dodecyl-1,4-napthoquinone (II) and polynactin (I) may contain from about 5 to 1000 ppm of total active ingredient. High volume sprays for field applications to vegetables or fruit trees may contain from about 10 to 800 ppm of active ingredient. Preferred high volume sprays for this use may contain from about 20 to 600 ppm of total active ingredient. Most preferred sprays for this use may contain from about 80 to 600 ppm of the two compounds.

Low volume or ultra low volume sprays may be desired when aerial applications are appropriate. Under such circumstances users can calculate concentrations to be applied based on a knowledge of their equipment and other considerations.

On an area basis in a field situation, from about 0.02–12.5 kg/ha of total active ingredient of these combinations should control most mite problems. It is preferable to use from about 0.05–7 kg/ha. Smaller amounts tend to be useful for mite control in greenhouse applications, due primarily to the significant level of protection provided to the chemicals against the deleterious effect of the weather, e.g., rainfall, sunlight, etc.

These mixtures are especially suited for protection of fruit-bearing trees, nut-bearing trees, ornamentals, vegetable crops, horicultural crops, which would include small fruits and berries and seed crops. Apple trees, peach trees, citrus, cotton, peanuts, beans, strawberries, and ornamentals are particularly susceptible to mite damage in the field; ornamentals, horticultural crops, vegetable crosp, are particularly susceptible to mite damage in a greenhouse. Consequently, the mixtures of the instant invention are particularly useful for protection in the previously mentioned areas.

The present invention is further illustrated by the following examples.

EXAMPLE 1

Bean plants in the two leaf stage were infested with 50-100 two-spotted mites (*Tetranychus urticae*) per leaf and sprayed to run-off with aqueous suspensions made by dissolving appropriately weighted quantities of polynactin (I) and 3-acetoxy-2-n-dodecyl-1,4-naphthoquinone (II) in 15 ml of acetone and diluting the mixture to the desired spray concentration with water containing Surfactant F (Trem 014)* at 1:3000. After spraying, the plants were held under greenhouse conditions for 2 weeks, i.e. 14 days. Mortality counts were made after 48 hours; mites per leaf were counted and plant injury ratings were made at the end of 2 weeks. The results were recorded in Table 1 below.

*Available from the Nopco Division of the Diamond Shamrock Co.

TABLE 1

| Conc. ppm | | % Kill | 2-Week Readings | |
|---|---|---|---|---|
| II | I | 48 Hrs. | Live Mites/Leaf | Feeding Injury[1] |
| 20 | — | 100 | 6 | 0 |
| 10 | — | 97 | 186 | 4 |
| 5 | — | 35 | 321 | 7 |
| — | 40 | 31 | 2 | 2 |
| — | 20 | 19 | 0 | 3.5 |
| — | 10 | 6 | 222 | 7 |
| 10 | 40 | 98 | 7 | 0 |
| 10 | 20 | 100 | 22 | 0 |
| 10 | 10 | 98 | 1 | 0 |
| 10 | 5 | 100 | 3 | 0 |
| 5 | 40 | 99 | 0 | Trace |
| 5 | 20 | 95 | 2 | 0 |
| 5 | 10 | 96 | 0 | 0 |
| 5 | 5 | 75 | 64 | Trace |

[1] 0 = No feeding; 10 = leaf destroyed.

EXAMPLE 2

Results for an experiment, similar in all respects to that described in Example 1, with the exception that counts of mites per leaf and feeding injury ratings were recorded at the end of 1 week, are as set forth in Table 2 below.

TABLE 2

| Conc. ppm | | % Kill | 1-Week Readings | |
|---|---|---|---|---|
| II | I | 48 Hrs. | Live Mites/Leaf | Feeding Injury[1] |
| 20 | — | 100 | 63 | Trace |
| 10 | — | 100 | 37 | 0.5 |
| 5 | — | 91 | 301 | 0.5 |
| — | 40 | 87 | 4 | 3 |
| — | 20 | 33 | 74 | 3 |
| — | 10 | 36 | >500 | 4 |
| — | 5 | 13 | >500 | 3 |
| 10 | 20 | 100 | 0 | 0.5 |
| 10 | 10 | 100 | 0 | Trace |
| 10 | 5 | 100 | 37 | Trace |
| 5 | 20 | 98 | 4 | 0.5 |
| 5 | 10 | 54 | 21 | Trace |
| 5 | 5 | 99 | 2 | Trace |

[1] 0 = no feeding; 10 = leaf destroyed.

EXAMPLE 3

Red kidney bean plants 7-9 days old were infested with two-spotted spider mites by placing on the plants leaf sections cut from infested plants. After 2-4 hours, 50-75 adult mites per leaf transferred to the fresh plants. Each of the infested plants was sprayed to run-off with 50 ml of the desired solution and then held, observing knockdown, 2-, 7-, and 14-day mortality, and plant injury.

The highest rates selected for testing were the minimum equivalent quantities of (I) and (II) which consistently produced a significant effect (Compound II-10 ppm; Polynactin-10 ppm). When testing combinations of these compounds not more than one-half of the minimum equivalent quantities were used in this test. Each test was run in duplicate; test results are reported in Tables 3 and 4.

TABLE 3

Control of the Two-Spotted Spider Mite on Beans with Polynactin, Compound II and Their Mixtures

| Treatment | ppm *ai | No. Knockdown | % Mortality Days | | | % Injury Due to Mite Feeding Compared to Check Days | | |
|---|---|---|---|---|---|---|---|---|
| | | | 2 | 7 | 14 | 2 | 7 | 14 |
| Check | — | 0 | 2 | 4 | 8 | — | — | — |
| Compound (II) | 10 | 125 | 100 | 100 | 76 | 0 | 0 | 10 |

TABLE 3-continued

Control of the Two-Spotted Spider Mite on Beans with Polynactin, Compound II and Their Mixtures

| Treatment | ppm *ai | No. Knockdown | % Mortality Days 2 | 7 | 14 | % Injury Due to Mite Feeding Compared to Check Days 2 | 7 | 14 |
|---|---|---|---|---|---|---|---|---|
| | 8 | 93 | 100 | 77 | 82 | 0 | 0 | 0 |
| | 6 | 92 | 93 | 61 | 19 | 10 | 10 | 100 |
| | 4 | 88 | 84 | 30 | 17 | 10 | 20 | 100 |
| | 2 | 8 | 28 | 4 | 6 | 30 | 50 | 100 |
| Polynactin | 10 | 8 | 16 | 70 | 75 | 60 | 100 | 100 |
| | 8 | 8 | 6 | 30 | 66 | 60 | 100 | 100 |
| | 6 | 0 | 5 | 39 | 50 | 80 | 100 | 100 |
| | 4 | 0 | 1 | 5 | 50 | 80 | 100 | 100 |
| | 2 | 0 | 2 | 5 | 50 | 80 | 100 | 100 |
| Check | — | 0 | 0 | 2 | 5 | — | — | — |
| Compound (II) + Polynactin | 5 + 1 | 92 | 97 | 97 | 49 | 0 | 0 | 20 |
| | 5 + 2 | 46 | 100 | 100 | 96 | 0 | 0 | 30 |
| | 5 + 3 | 55 | 99 | 100 | 100 | 0 | 0 | 10 |
| | 5 + 4 | 57 | 98 | 99 | 97 | 10 | 0 | 10 |
| | 5 + 5 | 49 | 100 | 100 | 100 | 0 | 0 | 10 |
| | 4 + 5 | 57 | 89 | 92 | 100 | 20 | 10 | 10 |
| | 3 + 5 | 25 | 56 | 16 | 93 | 40 | 40 | 50 |
| | 2 + 5 | 19 | 40 | 6 | 83 | 70 | 70 | 70 |
| | 1 + 5 | 2 | 6 | 3 | 50 | 80 | 100 | 100 |

*ai - active ingredient

TABLE 4

Control of the Two-Spotted Spider Mite on Beans with Polynactin, Compound II and Their Mixtures

| Treatment | ppm *ai | No. Knockdown | % Mortality Days 2 | 7 | 14 | % Injury Due to Mite Feeding Compared to Check Days 2 | 7 | 14 |
|---|---|---|---|---|---|---|---|---|
| Check | — | 0 | 0 | 4 | 7 | — | — | — |
| Compound (II) | 10 | 112 | 100 | 100 | 18 | 0 | 0 | 30 |
| | 8 | 156 | 100 | 90 | 30 | 0 | 0 | 10 |
| | 6 | 94 | 96 | 68 | 25 | 0 | 20 | 70 |
| | 4 | 77 | 86 | 21 | 20 | 10 | 30 | 70 |
| | 2 | 16 | 16 | 5 | — | 30 | 100 | 100 |
| Polynactin | 10 | 5 | 12 | 2 | 63 | 70 | 100 | 100 |
| | 8 | 5 | 5 | 9 | 54 | 80 | 100 | 100 |
| | 6 | 0 | 0 | 3 | — | 70 | 100 | 100 |
| | 4 | 0 | 2 | 2 | 50 | 70 | 100 | 100 |
| | 2 | 0 | 2 | 3 | 59 | 100 | 100 | 100 |
| Check | — | 0 | 0 | 2 | 4 | — | — | — |
| Compound (II) + Polynactin | 5 + 1 | 52 | 79 | 33 | 41 | 20 | 40 | 50 |
| | 5 + 2 | 56 | 69 | 51 | 52 | 20 | 20 | 30 |
| | 5 + 3 | 62 | 95 | 100 | 97 | 10 | 0 | 0 |
| | 5 + 4 | 44 | 87 | 97 | 98 | 10 | 0 | 10 |
| | 5 + 5 | 35 | 91 | 100 | 99 | 10 | 10 | 10 |
| | 4 + 5 | 32 | 84 | 94 | 98 | 10 | 10 | 10 |
| | 3 + 5 | 19 | 49 | 19 | 75 | 20 | 30 | 30 |
| | 2 + 5 | 12 | 25 | 7 | — | 60 | 100 | 100 |
| | 1 + 5 | 6 | 6 | 3 | 50 | 100 | 100 | 100 |

*ai - active ingredient

Figure 2:
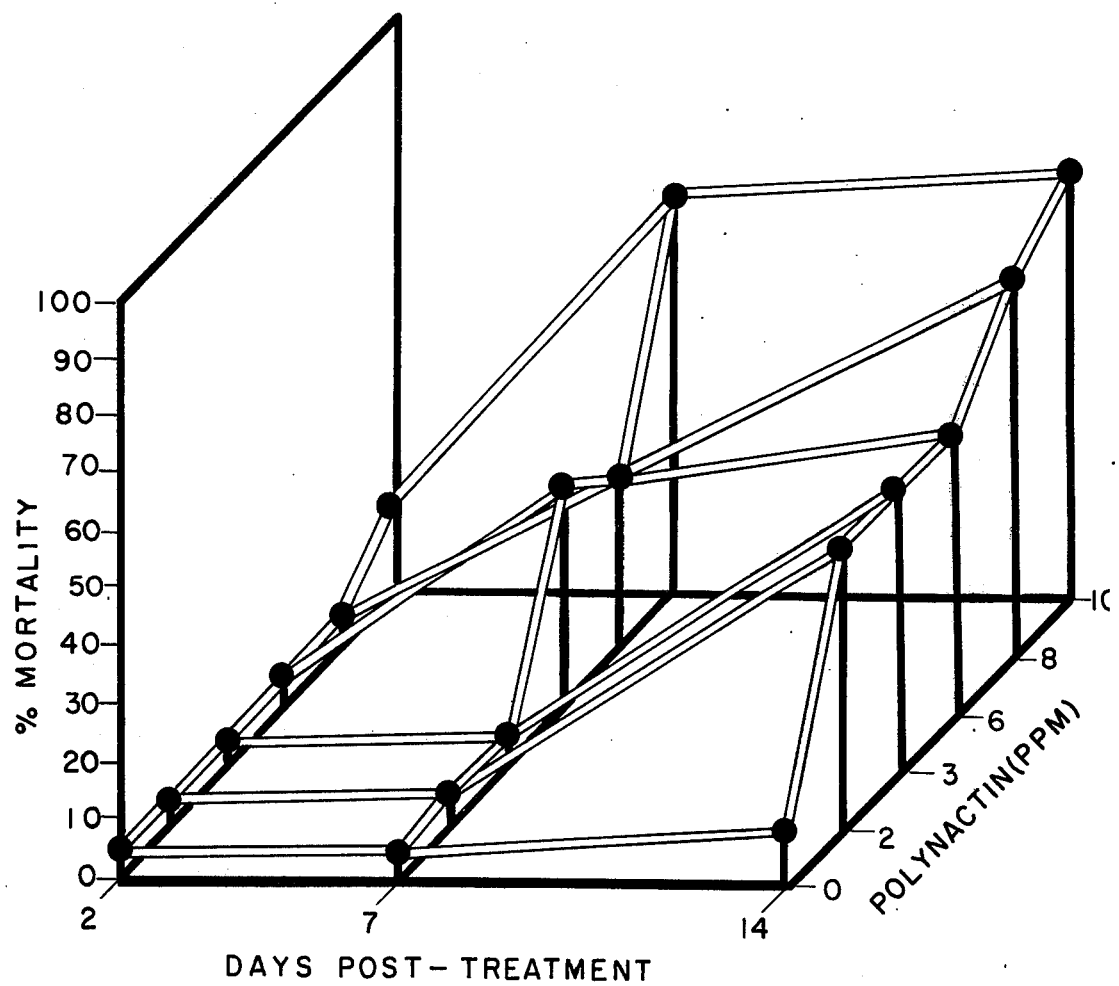
FIG. 2 is a three-dimensional graph showing mite mortality observed when polynactin (I) was applied individually to mite-infested plants.

FIGS. 1, 2, 3 and 4, represent in three-dimensional graphs the results of Example 3. FIGS. 1 and 2 illustrate the mite mortality observed when Compound (II) and polynactin were applied individually to mite-infested plants. Using 10 ppm of Compound (II), 100% control of adult mite is observed after 2 days, after which the compounds' activity diminishes. Mite eggs are not significantly affected by this rate of (II), and new adult mites produced therefrom cause the leaf injury observed after 7 and 14 days. In FIG. 2, at 10 ppm, polynactin only produces a 75% mite mortality after 7 days and 14 days.

Figure 3:
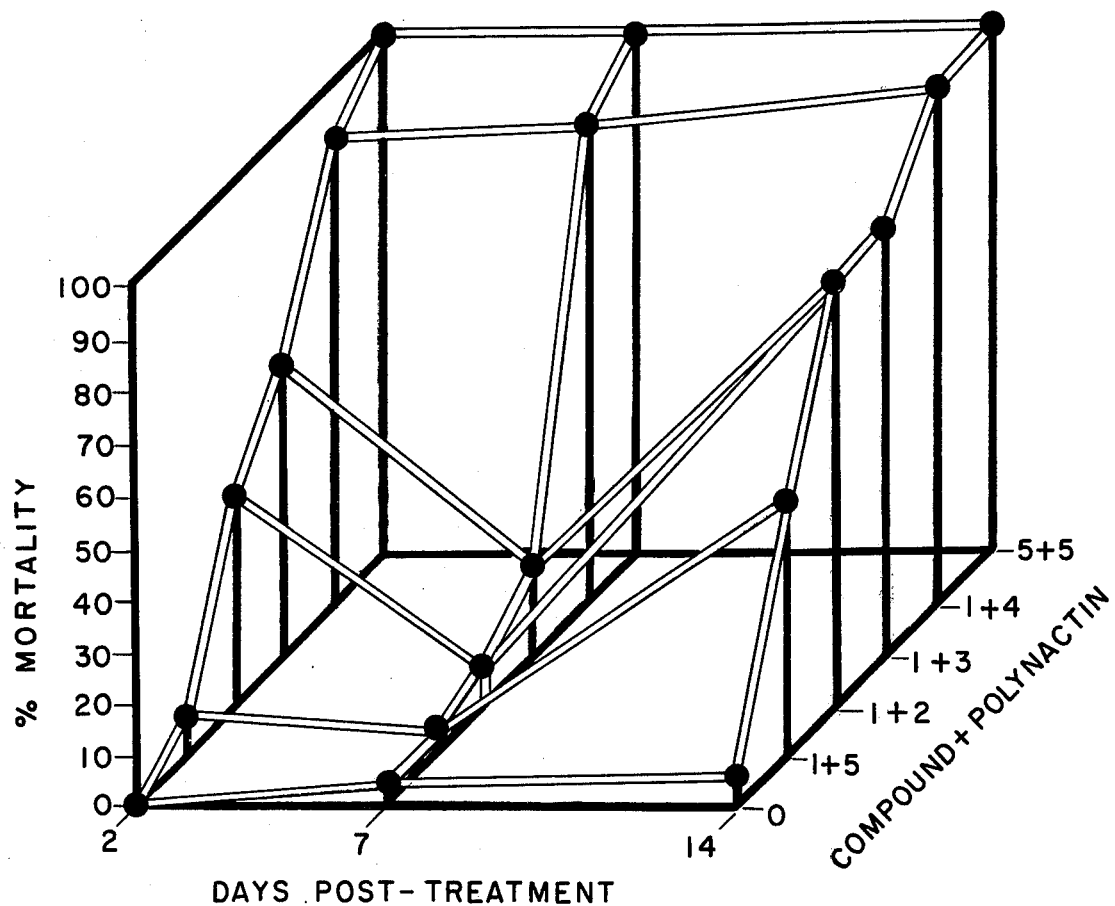
FIG. 3 is a three-dimensional graph showing mite mortality observed when mixtures of compound (II) and polynactin (I), the concentration of polynactin being held constant, were applied to mite-infested plants.

In FIG. 3, polynactin concentration of the mixture is held constant at 5 ppm while the concentration of Compound (II) is varied from 0–5 ppm. 100% Control of adult mites is observed after 2, 7 and 14 days where only 5 ppm of each ingredient is present in the mixture.

Figure 4:
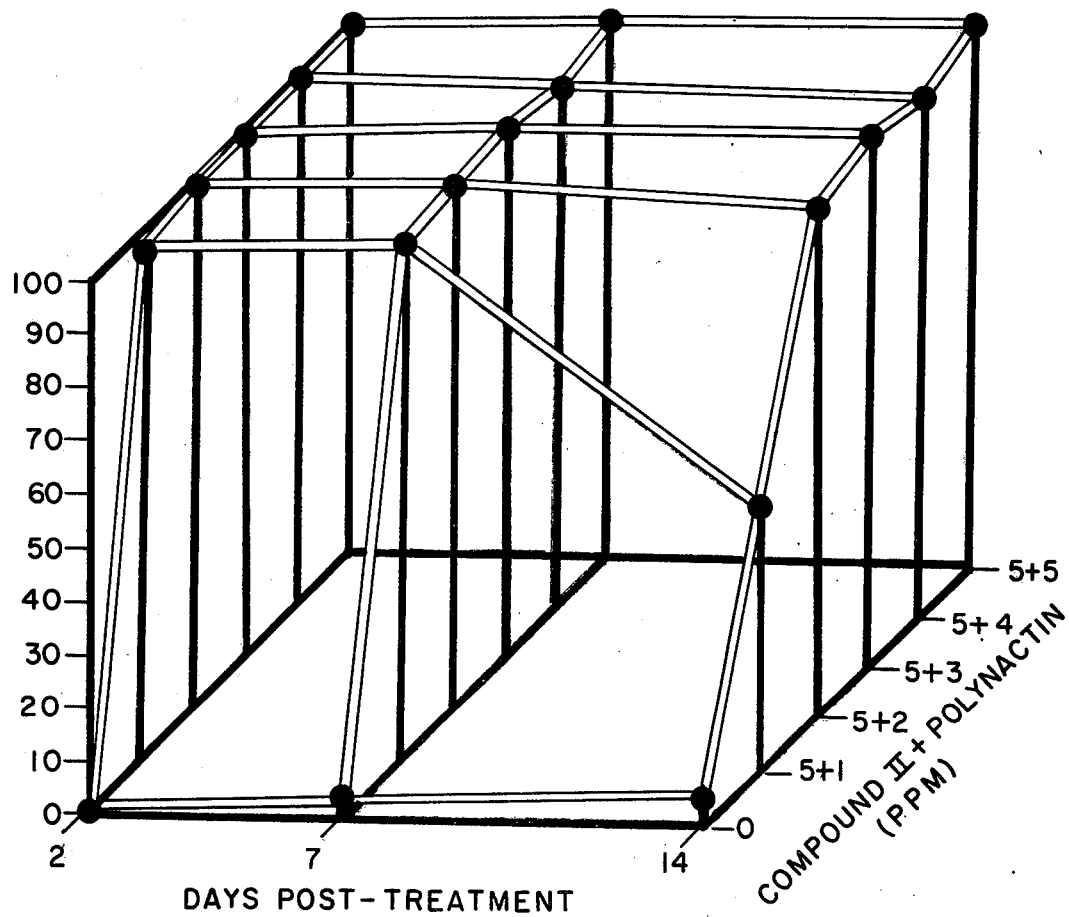
FIG. 4 is a three-dimensional graph showing mite mortality observed when mixtures of compound (II) and polynactin (I), the concentration of compound (II) being held constant, were applied to mite-infested plants.

In FIG. 4, synergism is even more evident. Using a mixture having a concentration of 5 ppm Compound (II) and only 1 ppm polynactin, 97% control of adult mites is observed after 2 and 7 days. Where the concentration of polynactin is increased to 2 ppm, and up to 5 ppm, nearly 100% control of adult mites is observed for each recording interval.

Biological activity is likely to vary for each compound depending upon the particular conditions encountered in the mite rearing and test situation. These factors include the amount and effect of light, minor variations in the mite colony, small differences in temperature and humidity, and the like. The exact ratio of polynactin to Compound (II) may, therefore, have to be adjusted over a broad range to obtain optimum mite control for a given species with the most economical mixture.

Useful formulations prepared containing mixtures of compounds (I) and (II) as active ingredient can be prepared in conventional ways. They include dusts, granules, pellets, solutions, suspensions, emulsions, wettable powders, emulsifiable concentrates and the like. Many of these may be applied directly. Sprayable formulations can be extended in suitable media and used as spray volumes of from a few pints to several hundred gallons per acre. High strength compositions are primarily used as intermediates for further formulation.

The formulations, broadly, contain about 1 to 99% by weight of active ingredient and at least one of (a) about 0.1% to 20% surfactants and (b) about 1% to 99% solid or liquid diluents. More specifically, they will contain these ingredients in the following approximate proportions:

|  | Total Active Ingredients | Percent by Weight | |
|---|---|---|---|
|  |  | Diluents | Surfactants |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th. Edn., McGraw-Hill, N.Y., 1963, pp. 8–59ff.

For further information regarding the art of formulation, see for example:
J. B. Buchanan, U.S. Pat. No. 3,576,834, Apr. 27, 1971, Col. 5 Line 36 through Col. 7 Line 70 and Ex. 1–4, 17, 106, 123–140.
R. R. Shaffer, U.S. Pat. No. 3,560,616, Feb. 2, 1971, Col. 3 Line 48 through Col. 7 Line 26 and Examples 3–9, 11–18.
E. Somers, "Formulation", Chapter 6 in Torgeson, "Fungicides", Vol. I, Academic Press, New York, 1967.

This invention is further illustrated by the following examples:

EXAMPLE 4

| Emulsifiable Concentrate | |
|---|---|
| 2-acetoxy-3-n-dodecyl-1,4-naphthoquinone (II) | 15% |
| polynactin (I) | 15% |
| blend of oil soluble sulfonates and polyoxyethylene ethers | 4% |
| xylene | 66% |

The ingredients are combined and sand-milled to produce a suspension. A fine screen filter is included in packaging operation to insure the absence of any extraneous undissolved material in the product.

EXAMPLE 5

| Wettable Powder | |
|---|---|
| 2-acetoxy-3-n-dodecyl-1,4-naphthoquinone (II) | 25% |
| polynactin (I) | 15% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All mixtures of the invention may be formulated in the same manner.

I claim:
1. A miticidally effective mixture consisting essentially of

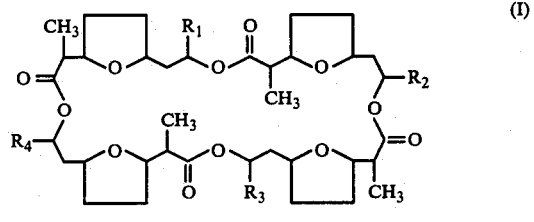

and

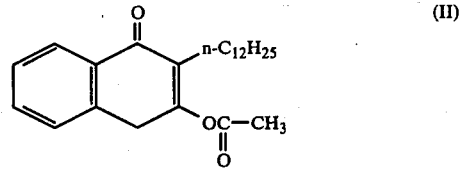

wherein
$R_1$, $R_2$, $R_3$ and $R_4$ are each selected from the group consisting of methyl and ethyl and the ratio of I to II is between 5:1 and 1:5.

2. A composition for the control of mites consisting essentially of a miticidally effective amount of the mixture of claim 1 and at least one of (1) a surface-active agent and (b) a solid or liquid diluent.

3. A method for protecting plants from mites comprising applying to the plant locus to be protected a miticidally effective amount of the mixture of claim 1.

* * * * *